United States Patent [19]

Micklethwaite et al.

[11] Patent Number: 5,250,736
[45] Date of Patent: Oct. 5, 1993

[54] METHOD OF PREPARING A PHOSPHINE COMPOUND

[75] Inventors: Colleen E. Micklethwaite; Allan J. Robertson, both of Thorold, Canada

[73] Assignee: Cyanamid Canada Inc., Markham, Canada

[21] Appl. No.: 927,998

[22] Filed: Aug. 11, 1992

[30] Foreign Application Priority Data

Oct. 30, 1991 [CA] Canada .............................. 2054546-1

[51] Int. Cl.$^5$ ............................................. C07F 9/50
[52] U.S. Cl. ........................................ 568/8; 568/9; 568/10; 568/17
[58] Field of Search ........................... 568/8, 9, 10, 17

[56] References Cited

U.S. PATENT DOCUMENTS 3,389,183  6/1965  Hays ........................................ 568/8

Primary Examiner—Marianne M. Cintins
Assistant Examiner—Margaret J. Page
Attorney, Agent, or Firm—Frank M. Van Riet

[57] ABSTRACT

Allylphosphines and vinylphosphines are prepared by reaction of a phosphine with an allylhalide or a vinylhalide, respectively. Preferably the phosphine is a secondary phosphine, so that there is formed an allyldialkylphosphine or a dialkylvinylphosphine. The allyldialkylphosphine can be reacted further with dialkylphosphine under free radical conditions to yield a 1,3-bis-(dialkylphosphino)propane. The dialkylvinylphosphine can be reacted further with dialkylphosphine under free radical conditions to yield a 1,2 bis-(dialkylphosphino)ethane. These compounds are useful as bidentate ligands.

16 Claims, No Drawings

METHOD OF PREPARING A PHOSPHINE COMPOUND

The present invention relates to a novel process for preparing allylphosphines and vinylphosphines.

Allylphosphines and vinylphosphines are useful intermediate compounds in the preparation of various phosphine compounds as final products. For instance the present invention provides a route, via the novel process for preparing allylphosphines and vinylphosphines, to 1,3-bis (phosphino)propanes and 1,2-bis-(phosphino)ethanes that find use as bidentate ligands. Such ligands are used in the preparation of reactive catalysts, for example rhodium/phosphine catalysts that are used for the decarbonylation of aldehydes to alkanes. Phosphine compounds also find use in flame retardants and as specialty solvents, for instance in solvent extraction processes.

The present invention provides a process for preparing an allylphosphine or a vinylphosphine, which process comprises reacting a phosphine with an allylhalide or a vinylhalide to form an allylphosphonium salt or a vinylphosphonium salt, respectively, followed by treatment with a base to convert the salt to the free allylphosphine or vinylphosphine base.

A preferred embodiment of the invention is the reaction of an allylhalide with a secondary phosphine to form an allyldialkylphosphine. The reaction is illustrated by the following equations

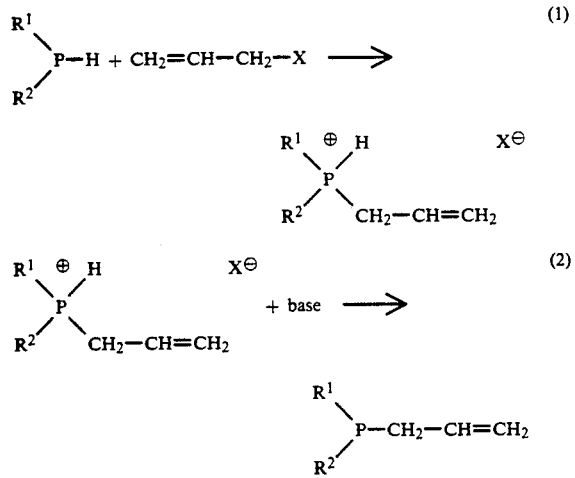

$R^1$ and $R^2$, which may be the same or different, can be selected from alkyl, aryl, alkaryl, aralkyl, cycloalkyl, alkylcycloalkyl, alkoxyalkyl, cycloalkylaryl, aminoalkyl, heterocyclyl and heterocyclylalkyl groups. The groups $R^1$ and $R^2$ can also be alkenyl, provided that the double bond is not terminal. Terminal double bonds in $R^1$ and $R^2$ would cause unwanted reactions, leading to undesired mixtures of products. The various radicals can be substituted provided that the substituents do not interfere with the reaction. A person skilled in the art will know whether a substituent will interfere, or will be able to determine this by routine experiment without exercise of any inventive faculty. Examples of suitable values for $R^1$ and $R^2$ include, but are not limited to methyl; ethyl; n-propyl; isopropyl; n-butyl; isobutyl; n-pentyl; n-hexyl; n-heptyl; n-octyl; n-nonyl; n-decyl; n-dodecyl; n-tetradecyl; n-hexadecyl; n-eicosyl; 2,4,4-trimethylpentyl; cyclopentyl; cyclohexyl; cyclooctyl; cyclooctyl ether; 2,4,6-triisopropyl-1,3,5-dioxaphosphorinane, phenyl; p-chloropenyl; o-tolyl; m-tolyl; p-tolyl; 2,3-dimethylphenyl; 2,4-dimethylphenyl; 2,5-dimethylphenyl; 2,6-dimethylphenyl; 3,4-dimethylphenyl; 3,5-dimethylphenyl; p-ethylphenyl; p-octylphenyl; n-butylphenyl; n-octylphenyl; n-hexadecylphenyl; o-chlorophenyl; m-chlorophenyl; p-chlorophenyl; benzyl; naphthyl; 1-hydroxycyclohexyl; 2-methyl-1-hydroxypentyl; alpha-hydroxybenzyl; o-chlorobenzyl, alpha-hydroxy-o-chlorobenzyl; p-chlorobenzyl, alpha-hydroxy-p-chlorobenzyl; alpha-methylbenzyl; 1-hydroxycyclopentyl; alpha-hydroxy-alpha-methylbenzyl; 1-methylpentyl; 1-hydroxy-1-methylpentyl; alpha-hydroxybenzyl; (1-hydroxy-1-methylethyl)isopropyl.

In the description of the invention there occur references to alkyl groups, for instance in the terms allyldialkylphosphine and dialkylvinylphosphine. It will be understood that the groups referred to are the groups $R^1$ and $R^2$ and that the term "alkyl" is not necessarily being used in a strict sense to mean a radical obtained by removal of a hydrogen atom from an alkane. Whether the term "alkyl" is being used in a loose or a strict sense will be apparent from the context.

The reaction of a secondary phosphine with an allylhalide is preferably carried out in solution. The secondary phosphine is dissolved in an organic, nonpolar solvent and the allylhalide is added gradually. In general, the reaction can take place at room temperature but it is preferred to use elevated temperature. If the reaction is run at low temperature the addition of allylhalide must be slow, to avoid a buildup of allylhalide that could cause a runaway reaction. If the temperature is too high the allylhalide may boil and be in gaseous form above the reaction mixture, thus slowing the reaction. If operating at atmospheric pressure a temperature in the range of about 60° to 80° C. is preferred. It is possible to carry out the reaction in an autoclave at autogenous pressure, in which case a temperature of up to about 150° C. or higher can be used.

The organic, nonpolar solvent should be chosen with regard to its boiling point and also the boiling point of the required allyldialkylphosphine. If the selected solvent has a boiling point about 10° to 30° C., preferably about 10° to 20° C. higher than that of the required product this assists in separation of the product by distillation from unreacted starting materials. Mention is made of tetradecane, octadecane, eicosane and docosane as suitable nonpolar solvents.

Of the allylhalides, allylchloride reacts slowly with secondary phosphines. Allylbromide and allyliodide react more rapidly, and allylbromide is cheaper than allyliodide. Consequently allylbromide is preferred. Similarly, when using a vinylhalide vinylbromide is preferred.

In a preferred embodiment acetonitrile is also present in the reaction mixture. It has surprisingly been found that acetonitrile has the effect of greatly increasing the rate of reaction between a secondary phosphine and an allylhalide. The acetonitrile also assists in maintaining the phosphonium salt intermediate in solution. It also assists in separation of the final product. Water is added to the reaction mixture after reaction between the secondary phosphine and allylhalide and before addition of the base. Thereafter, the base is added. Acetonitrile is not miscible with nonpolar, hydrocarbon solvents Acetonitrile is normally miscible with water, but if the water contains a large quantity of ions the acetonitrile is not miscible but is salted out. Addition of the base results in salting out of the acetonitrile, so that there form three separate layers, an upper hydrocarbon layer, an intermediate acetonitrile layer and a lower aqueous layer.

The allyldialkylphosphine product is in the upper organic solvent. The halide salt formed by reaction between the added base and the phosphonium salt is present in the aqueous layer. It is found that impurities collect in the acetonitrile layer. If the phosphorus atom becomes oxidized to a phosphine oxide the phosphine oxide collects in the acetonitrile, so that it is separated from the unoxidized phosphine. When using allyl bromide, it is possible to use technical grade allylbromide, rather than analytical grade allylbromide, as it is observed that coloured impurities in the allylbromide migrate into the acetonitrile.

Other solvents can be used in place of acetonitrile, provided that they are not miscible with the organic solvent and can be salted out of the aqueous layer. Mention is made of propionitrile and methanol.

The three layers, i.e., the nonpolar solvent layer acetonitrile layer and aqueous layer, are readily separated. The allyldialkylphosphine product can be recovered from the nonpolar solvent by distillation. The acetonitrile can be recycled to the reaction after it has been treated to prevent buildup of impurities.

Although the preferred embodiment of the invention makes use of an allylhalide that is allyl in the strict sense, i.e., that contains the radical of formula $CH_2=CH-CH_2-$, it is within the scope of the invention to use a substituted allylhalide. The allyl radical can be substituted by a lower alkyl group, for instance a methyl group, on the 1- or 2- carbon atom, to give radicals of formula

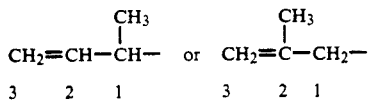

The allyl radical can be mono- or di-substituted on the 3-carbon atom by one or two alkyl groups. The alkyl group or groups can be long or short chained and can be branched, although long chains substituents may slow the rate of reaction. Any alkyl substituent on the 3-carbon atom can itself be substituted provided that the substituents do not interfere with the course of reaction. The person skilled in the art will know what substituents can be present, or will be able to determine this by routine experiment without exercise of any inventive faculty.

If the allyldialkylphosphine is to be further reacted with a phosphine to form a 1,3-bis-(dialkylphosphino)-propane, as described below, the allyl radical cannot be substituted on the 3-carbon atom. Products obtained from 3-substituted allyl radicals do not have a terminal double bond. A terminal double bond is essential for the further free radical reaction with a phosphine.

Similar remarks apply in respect of a vinylhalide. The vinylhalide may be substituted on the 1- or 2-carbon atoms, but should not be substituted on the 2-carbon atom if the product is to be further reacted with a phosphine.

In principle, any base can be used to convert the phosphonium salt to the free base. Inorganic bases that can be used include sodium hydroxide, potassium hydroxide, sodium carbonate, potassium carbonate, sodium hydrogen carbonate, potassium hydrogen carbonate, sodium ethoxide, potassium ethoxide, ammonium carbon ate, ammonium hydrogen carbonate, calcium oxide, calcium hydroxide, magnesium oxide and magnesium hydroxide. Organic bases that can be used are amines, particularly tertiary amines such as triethylamine. Of these bases, sodium carbonate and sodium hydrogen carbonate are preferred in view of their relative cheapness and also in view of the fact that the anion of the base forms $CO_2$ gas in the neutralization reaction, so that the product is not contaminated with any anion. The sodium cation forms a sodium halide salt that can be separated in aqueous solution from the organic solvent in which the free phosphine base dissolves. In contrast, if an organic base is used it may be necessary to carry out a separation step to remove the amine salt formed, depending upon the use to which the free phosphine base is to be put.

The invention has been described with reference to the reaction of a secondary phosphine with an allylhalide, preferably allylbromide. It should be appreciated that the process of the invention can be carried out with a primary phosphine, or with phosphine itself. If a primary phosphine is used there can be obtained two products, depending upon whether one or two hydrogen atoms of the primary phosphine are replaced by allyl groups. If phosphine itself is used then there are three hydrogen atoms that can be replaced by allyl groups so that in theory there are three possible products. In fact there will be formed a mixture of diallyl and triallyl products.

The reaction of a primary phosphine, or of phosphine itself, with an allylhalide proceeds, in general, in a similar manner to the reaction of a secondary phosphine with an allylhalide. The reaction proceeds more slowly, however, so it is preferred to carry out the reaction at elevated temperature in an autoclave. This is essential with phosphine itself, which is a gas at normal temperature and pressure.

A vinylhalide can be used in place of an allylhalide. Vinyl compounds usually display less reactivity than allyl compounds. To achieve reasonable reaction rates it is again preferred to operate at an elevated temperature in an autoclave. The preferred vinylhalide is the bromide.

In a preferred embodiment of the invention an obtained allyldialkylphosphine or dialkylvinylphosphine is subjected to a further reaction with a phosphine under free radical conditions. Free radical initiators that can be used include the known azo initiators such as azobisisobuyronitrile, azobisisovaleronitrile and the like 67. A covalent bond forms between the terminal carbon atom of the allyl moiety and the phosphorus atom of the phosphine. The reaction of an allyldialkylphosphine is illustrated by the following equation.

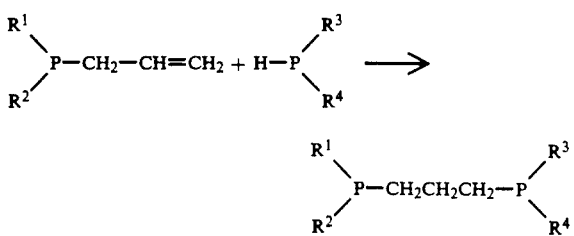

Thus there is formed a 1,3-bis-(dialkylphosphino)propane. A dialkylvinylphosphine forms a 1,2-bis-(dialkylphosphino)ethane. In the formulae $R^1$ and $R^2$ are as defined above. $R^3$ and $R^4$, which may be the same or different, can have the same values as $R^1$ and $R^2$ or can be hydrogen, i.e., the compound $R^3R^4PH$ can be phosphine itself or it can be a primary or secondary phosphine. If $R^3$ and $R^4$ do have the same values as $R^1$ and $R^2$ then the 1,3-bis-(dialkylphosphino)propane product will be a symmetrical compound; if $R^3$ and $R^4$ do not have the same values as $R^1$ and $R^2$ then the product will be an asymmetrical compound. Hence, the invention provides a route to symmetrical and asymmetrical 1,3-bis-(dialkylphosphino)propanes and also to symmetrical and asymmetrical 1,2-bis(phosphino)ethanes.

The phosphorus atom of a phosphine group is readily oxidized to form a phosphine oxide. Depending upon the use intended for the product, the presence of phosphine oxide may be undesirable. Oxidation can be avoided by means of careful handling procedures known to those skilled in the art. For instance, reactions can be carried out under inert gas and solutions purged with inert gas, for instance nitrogen.

The invention is further illustrated in the following examples

EXAMPLE 1

Diisobutylphosphine (176 g), acetonitrile (55 g) and tetradecane (59 g) were charged into a one liter reactor. The mixture was heated to 70° C. before allylbromide (131 g) was fed into the reactor over two hours. After the allylbromide was completely added, the solution was heated at 70° C. for one hour. The reaction solution was cooled to 40° C. and nitrogen purged water (250 g) was added. Sodium hydrogen carbonate (84 g) was slowly added to neutralize the phosphonium salt. When $CO_2$ evolution ceased, the water layer and acetonitrile layer were removed. The organic layer was washed with nitrogen purged water (250 g) and the water layer removed.

EXAMPLE 2

Dicyclohexylphosphine (446 g), acetonitrile (106 g), tetradecane (52 g) and eicosane (100 g) were charged into a one liter reactor. The mixture was heated to 70° C. Allylbromide (229 g) was added over two hours and once the charge was complete, the reaction mixture was heated for an hour at 70° C. Nitrogen purged water (250 g) was added to the cooled reaction at 40° C. Sodium hydrogen carbonate (151 g) was slowly charged over two hours. When the $CO_2$ evolution ceased, the water layer and acetonitrile layer were removed. The organic layer was washed once with nitrogen purged water (250 g).

EXAMPLE 3

Disecbutylphosphine (248 g), acetonitrile (114 g) and tetradecane (107 g) were combined in a one liter reactor. The reactor was heated to 70° C. Allylbromide (190 g) was added over 2.5 hours and when the charge was complete, the mixture was heated at 70° C. for one hour. When the reactor was cooled to 40° C., nitrogen purged water (250 g) was added. Sodium hydrogen carbonate (140 g) was slowly added over 2.5 hours. When the carbon dioxide evolution ceased, the water layer and acetonitrile layers were removed. The organic layer was washed with nitrogen purged water (250 g).

EXAMPLE 4

Dihexylphosphine (288 g), acetonitrile (108 g) and octadecane (120 g) were combined in a one liter reactor. The reactor was heated to 70° C. Allylbromide (179 g) was charged into the reactor over two hours. After the charge was complete, the reaction was heated at 70° C. for one hour. The mixture was cooled to 40° C. and nitrogen purged water (250 g) was added. Sodium hydrogen carbonate (121 g) was slowly added over three hours. When the $CO_2$ evolution finished, the water and acetonitrile layers were removed. Nitrogen purged water (250 g) was used to wash the remaining organic layer.

EXAMPLE 5

Dicyclopentylphosphine (434 g), acetonitrile (118 g) and hexadecane (51 g) were added to a one liter reactor. The mixture was heated to 70° C. before allylbromide (302 g) was added over 2.5 hours. The reaction mixture was heated at 70° C. for one hour after the allylbromide charge was complete. The reaction mixture was cooled to 40° C. Nitrogen purged water (250 g) was added before sodium hydrogen carbonate (212 g) was slowly added over four hours. Once the carbon dioxide evolution ceased, the water and acetonitrile layers were removed. The organic layer was washed with nitrogen purged water (250 g).

The organic layers from each of Examples 1 to 5 were subjected to analysis by gas chromatography, the nonpolar organic solvent being used as an internal standard (ISTD). The results are given in Table 1.

TABLE 1

| | GC Analysis of Final Reaction Product Mixture (Organic Layer) | | | | |
|---|---|---|---|---|---|
| | | | | GC analysis of final product organic layer (area %) | |
| Example No. | R | R' | hydrocarbon (ISID) | $R_2PH$ | $R_2PR^3$ |
| 1 | iso-butyl | allyl | tetradecane 26.3% | 10.8% | 60.8% |
| 2 | cyclohexyl | allyl | tetradecane 10.2% | 18.6% | 48.7% |
| 3 | sec-butyl | allyl | tetradecane 28.8% | 2.6% | 50.8% |
| 4 | hexyl | allyl | octadecane 30.7% | 2.9% | 57.5% |
| 5 | cyclopentyl | allyl | hexadecane 12.3% | 8.0% | 75.0% |

The results obtained are not strictly quantitative, but they do indicate relative amounts of compounds present in the organic layer. For instance, the results indicate that the organic layer from Example 1 contained approximately six times as much of $R_2PR'$, i.e., the product allyldiisobutylphosphine, as $R_2PH$, i.e., the starting material diisobutylphosphine.

EXAMPLES 6 TO 9

A reactor was charged with diisobutylphosphine (DIBP), acetonitrile and tetradecane. Allylbromide was then added over a period of time at a desired temperature, the particular times and temperatures being given in Table 2 and the particular amounts used being given in Table 3.

TABLE 2

Reaction Conditions for DIBP/Allylbromide Reaction Study

| Example No. | Temp. (°C.) | Allylbromide Addition Time (min.) |
| --- | --- | --- |
| 6 | 60–70 | 65 |
| 7 | 75–85 | 50 |
| 8 | 65–70 | 82 |
| 9 | 80–85 | 72 |

TABLE 3

Charges for DIBP/Allylbromide Reaction Study

| Example No. | DIBP | Allyl-bromide | Tetra-decane | Aceto-nitrile | NaHCO$_3$ |
| --- | --- | --- | --- | --- | --- |
| 6 | 157.3 | 122.0 | 50.5 | 66.8 | 83.0 |
| 7 | 161.5 | 121.5 | 49.2 | 50.8 | 82.6 |
| 8 | 163.3 | 126.3 | 55.0 | 55.3 | 84.9 |
| 9 | 716.1 | 130.5 | 58.8 | 54.7 | 83.4 |

After addition of the allylbromide the mixtures were held at the reaction temperatures for one hour and then cooled to 40° C. Water (200 g) was added, followed by slow addition of one equivalent of sodium hydrogen carbonate. The allyldiisobutylphosphine was liberated from the salt. Sodium bromide dissolved in the lower aqueous phase while the allyldiisobutylphosphine and any unreacted DIBP accumulated in the upper organic layer. Acetonitrile was found to some extent in both layers, but mostly as a small third layer between the upper organic layer and the lower aqueous salt solution. After decanting the aqueous layer the organic layer was washed with 150–200 mLs of water. At this point the acetonitrile dissolved in the aqueous phase.

The products were analysed by $^{31}$P NMR, gas chromatography and mass spectroscopy.

EXAMPLE 10

The organic layers from Examples 6 to 9 were combined (949.6 g) and charged to a stirred reactor. A free radical initiator (Vazo 67, 22.8 g) was added, together with additional DIBP (558.5 g). The mixture was heated for 21 hrs (overnight) at 73° C. Samples were taken throughout the run and subjected to gas chromatographic analysis, to follow the progress of the conversion to 1,3-bis-(diisobutylphosphino)propane.

The product mixture was vacuum stripped to remove unwanted reagents and tetradecane. The final vapour temperature was 149.5° C. at a pressure of 3.1 mm Hg. At this point the 1,3-bis(diisobutylphosphino)propane began to distil over.

EXAMPLES 11 TO 15

The procedures of Examples 6 to 9 were followed with allylbromide and different dialkylphosphines and solvents, in a first stage to form allyldialkylphosphines. The obtained allyldialkylphosphines were then subjected to a second stage reaction, in accordance with the procedure of Example 10. In each of the second stages the dialkylphosphine added was the same dialkylphosphine that had been used in the first stage, so that the product of each example was a symmetrical 1,3-bis-(dialkylphosphino)propane. The progress of the reactions and the identity of the products were monitored by gas chromatography and mass spectroscopy. The reaction conditions and results are given in Table 4.

TABLE 4

Charges and Reaction Conditions for the Preparation of 1,3-bis-(dialkylphosphino)propanes

| | Example No. | | | | |
| --- | --- | --- | --- | --- | --- |
| | 11 | 12 | 13 | 14 | 15 |
| R$^1$, R$^2$ | n-hexyl | n-hexyl | n-octyl | cy-pentyl | s-butyl |
| Hydrocarbon diluent | octadecane | octadecane | docosane | hexadecane | tetradecane |
| First Stage | | | | | |
| Allylbromide (g) | 179.3 | 196.3 | 198.1 | 301.5 | 211.2 |
| dialkylphosphine (g) | 287.2 | 307.7 | 407.5 | 434.2 | 248.0 |
| hydrocarbon (g) | 120.0 | 92.0 | 97.8 | 116.1 | 107.2 |
| acetonitrile (g) | 108 | — | — | 53.9 | 114.6 |
| NaHCO$_3$ (g) | 121.5 | 148.5 | 135.5 | 211 | |
| Temperature (°C.) | 70–75 | 72–79 | 70–80 | 75 | 73–74 |
| *Time (hr) | 2.0 | 2.3 | 2.5 | 2.7 | 2.5 |
| Second Stage | | | | | |
| dialkylphosphine (g) | 289.7 | 279.7 | 156.5 | 409.5 | 240.0 |
| VAZO 67 (g) | 18.4 | 18.5 | 17.9 | 15.7 | 10.2 |
| Temperature (°C.) | 70 | 75 | 73 | 72 | 71 |
| **Time (hr.) | 24 | 16 | 18 | 22 | 23 |

*Addition of allylbromide
**Overnight reactions. The actual reaction time may be less

We claim:

1. A process for preparing an allylphosphine or a vinylphosphine which comprises reacting, in the presence of acetonitrile and a nonpolar organic solvent, a phosphine with an allylhalide or a vinylhalide to form an allylphosphonium salt or a vinyl phosphonium salt, respectively, followed by treatment with a base to convert the phosphonium salt to the free allylphosphine or vinylphosphine base.

2. A process as claimed in claim 1 wherein a secondary phosphine is reacted with an allylhalide.

3. A process as claimed in claim 1 wherein a secondary phosphine is reacted with a vinylhalide.

4. A process as claimed in claim 2 wherein the allylhalide is allylbromide.

5. A process as claimed in claim 3 wherein the vinylhalide is vinylbromide.

6. A process as claimed in any one of claims 1 to 5 wherein the phosphine is diisobutylphosphine, dicyclohexylphosphine, di-n-hexylphosphine, dicyclopentylphosphine or di-n-octylphosphine.

7. A process as claimed in claim 6 wherein the base is sodium carbonate, sodium hydrogen carbonate, ammonium carbonate or ammonium hydrogen carbonate.

8. A process as claimed in claim 1 wherein the reaction is carried out in a nonpolar organic solvent whose boiling point is about 20° to 30° C. higher than the boiling point of the required allylphosphine or vinylphosphine.

9. A process as claimed in claim 1 wherein the reaction is carried out in tetradecane, hexadecane, octadecane, docosane, or eicosane.

10. A process as claimed in any one of claims 1 to 5, 8 and 10 wherein water is added to the reaction mixture after the base.

11. A process as claimed in claim 10 wherein the base is sodium hydrogen carbonate.

12. A process as claimed in any one of claims 1 to 5, 7, 9, 10 and 11 wherein an obtained allylphosphine or vinyl phosphine each containing a terminal double bond is subjected to further reaction with a phosphine under free radical conditions.

13. A process as claimed in any one of claims 1 to 5, 8, 10, and 12 wherein a dialkylphosphine is reacted with an allylbromide to form an allyldialkylphosphine that is reacted further with a dialkylphosphine under free radical conditions, so that there is formed a 1,3-bis-(dialkylphosphino)propane.

14. A process as claimed in claim 13 wherein the dialkylphosphine that is reacted with the allylbromide is the same as the dialkylphosphine reacted with the allyldialkylphosphine, so that there is formed a symmetrical 1,3-bis-(dialkylphosphino)propane.

15. A process as claimed in any one of claims 1 to 5, 8, 9, and 14 wherein a dialkylphosphine is reacted with a vinylbromide to form a dialkylvinylphosphine that is reacted further with a dialkylphosphine under free radical conditions, so that there is formed a 1,2-bis-(dialkylphosphino)ethane.

16. A process as claimed in claim 15 wherein the dialkylphosphine that is reacted with the vinylbromide is the same as the dialkylphosphine reacted with the dialkylvinylphosphine, so that there is formed a symmetrical 1,2-bis-(dialkylphosphino)ethane.

* * * * *